United States Patent
Flot

(10) Patent No.: US 6,268,589 B1
(45) Date of Patent: Jul. 31, 2001

(54) CONTROLLER AND STERILIZABLE HEAD FOR A DEVICE FOR HEATING CLIPS WITH SHAPE MEMORY

(75) Inventor: Francis Flot, Nancy (FR)

(73) Assignee: M.B.A., S.A., Vandoeuvre (FR)

(*) Notice: Subject to any disclaimer, the term of this patent is extended or adjusted under 35 U.S.C. 154(b) by 0 days.

(21) Appl. No.: 09/462,862
(22) PCT Filed: May 14, 1999
(86) PCT No.: PCT/FR99/01150
 § 371 Date: Jan. 14, 2000
 § 102(e) Date: Jan. 14, 2000
(87) PCT Pub. No.: WO99/59478
 PCT Pub. Date: Nov. 25, 1999

(30) Foreign Application Priority Data

May 15, 1998 (FR) .................................. 98 06341
May 7, 1999 (FR) .................................. 99 06042

(51) Int. Cl.⁷ .............................. H05B 3/42; A61M 29/00
(52) U.S. Cl. .................... 219/229; 219/201; 219/221; 219/227; 219/230; 606/78; 606/194; 606/219
(58) Field of Search .................... 219/201, 221, 219/227, 228, 229, 230, 231, 232, 233, 234, 235, 240, 241, 243, 248, 250, 251, 252, 253; 606/219, 78, 215, 216, 227, 151, 157, 158, 194, 108, 198; 128/334, 899

(56) References Cited

U.S. PATENT DOCUMENTS

| | | |
|---|---|---|
| 3,868,956 | 3/1975 | Alfidi et al. . |
| 4,485,816 | 12/1984 | Krumme . |
| 4,550,870 | 11/1985 | Krumme et al. . |
| 4,665,906 | 5/1987 | Jervis ........................ 606/78 |
| 5,067,957 | 11/1991 | Jervis ........................ 606/108 |
| 5,190,546 | 3/1993 | Jervis ........................ 606/78 |
| 5,597,378 | 1/1997 | Jervis ........................ 606/78 |

FOREIGN PATENT DOCUMENTS

| | | |
|---|---|---|
| 2747911 | 10/1997 | (FR) . |
| WO 9616603 | 6/1996 | (WO) . |

Primary Examiner—Tu Ba Hoang
(74) Attorney, Agent, or Firm—Gary M. Cohen

(57) ABSTRACT

A device for heating and closing heat-retractable clamps for surgical use includes a housing which encloses an electronic power and control circuit, a power cord connected to the circuit, and a heating unit for applying heat to the clamps. The electronic power and control circuit includes a power supply, a controller and a regulating circuit for delivering different predetermined amounts of heat, each corresponding to a clamp of a given size. The heating unit is capable of being sterilized in an autoclave and includes a linking cord, one end of which is capable of being plugged into the housing for the electronic circuit and the other end of which is coupled with a sleeve having a pair of electrodes and a control switch for operating the electrodes.

23 Claims, 2 Drawing Sheets

CONTROLLER AND STERILIZABLE HEAD FOR A DEVICE FOR HEATING CLIPS WITH SHAPE MEMORY

BACKGROUND OF THE INVENTION

The present invention generally relates to devices for heating and closing heat-retractable shape memory clamps used in surgery applications.

More particularly, the present invention relates to a device for heating and closing nickel/titanium alloy clamps known as "hot clamps". Such clamps are initially open at ambient temperature, for purposes of placement. A quantity of heat is then provided to close the positioned clamp and thus provide tissue support.

In practice, the ergonomic and economic standardization of surgical constraints requires such clamps to be manufactured to extremely restrictive specifications.

In this context, it is important for the device to be able to close all types of clamps, whether they be mono-cortical or bicortical, bipode or quadripode clamps, and irrespective of their section. It is also important for the device to include a reliable and effective safety system to prevent accidental bone necroses due to the heat applied by the device. It is also important for the device to have a heating cord that can be sterilized in an autoclave or disinfected in a bath.

SUMMARY OF THE INVENTION

Such goals are achieved in accordance with the present invention by providing a device for heating and closing heat-retractable shape memory clamps used in surgery applications which is generally comprised of a unit which contains an electronic power and control circuit and a heating unit.

The electronic power and control circuit is preferably comprised of a current supply, a controller and an adjustment circuit which combine to deliver several predetermined quantities of heat, each corresponding to a given size of clamp.

Primarily for purposes of safety, the adjustment circuit is configured (calculated) so that the amount of heat delivered to a given clamp does not cause the temperature of the clamp to exceed a maximum value, such as 55° C. Also for purposes of safety, the electronic circuit further includes an automatic cut-out circuit for discontinuing the application of heating current at the end of a predetermined maximum time, such as 5 seconds, and a sound signalling circuit for emitting a first sound as a signal during the application of heat to the clamp (the heating time) and a second sound which differs from the first sound as a signal that the maximum heating time has been exceeded.

The heating unit is preferably constructed as a sterilizable unit. One end of the heating unit has a plug which can be plugged into a corresponding outlet of the device and the other end of the heating unit has a sleeve which includes a pair of heating electrodes and a control switch. The sterilizable unit is fully sealed and the several elements which comprise the sterilizable unit are selected to withstand the conditions of an autoclave. In its preferred embodiment, the control switch is provided with pressure-sensitive contacts.

The present invention shall be more readily understood from the following description, with reference to the accompanying drawings.

DETAILED DESCRIPTION OF THE INVENTION

Figure 1:
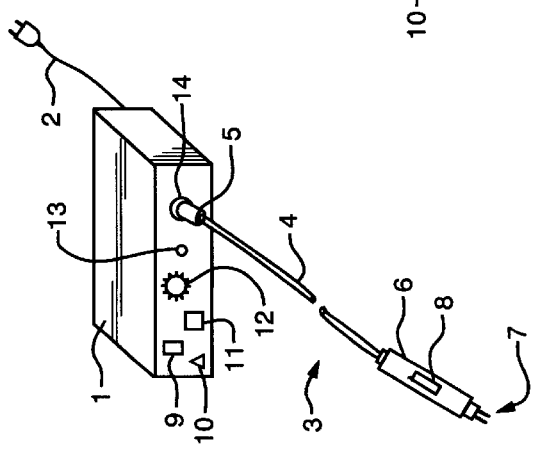
FIG. 1 is an isometric view of the device of the present invention.

As shown in FIG. 1, the device of the present invention is generally comprised of a box (1) containing an electronic power and control circuit (to be described below), a main power supply cord (2) for connecting the box (1) to a power source (i.e., line current), and a sterilizable unit (3). The sterilizable unit (3) is formed as a linking cord (4), one end of which has a plug (5) which can be plugged into an outlet (14) of the box (1) and the other end of which has a sleeve (6) which includes two heating electrodes (7) and a control switch (8).

Figure 5:
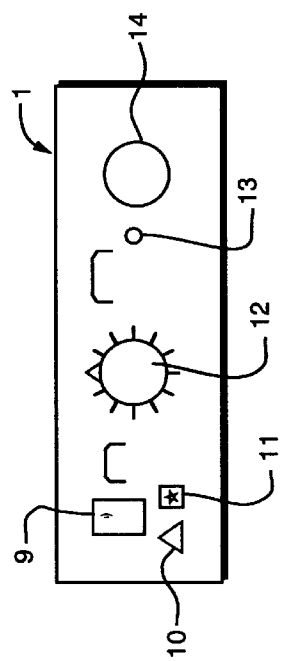
FIG. 5 is an elevational view of the front face of the device shown in FIG. 1.

Referring to FIG. 5, the front face of the box (1) is equipped with a main switch (9), a luminous defect indicator light (10), a luminous "on" signal indicator light (11), a heat quantity adjustment (potentiometer) knob (12), an indicator light (13) for signalling heating of the electrodes (7) and the outlet plug (14) for receiving the sterilizable unit (3). The rear face (not shown) of the box (1) is conventionally equipped with a signalling plate and an outlet for the supply cord (2).

Figure 2:
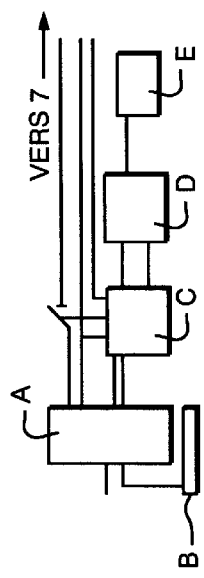
FIG. 2 is a block diagram of the electronic circuit of the device of the present invention.
Figure 3:
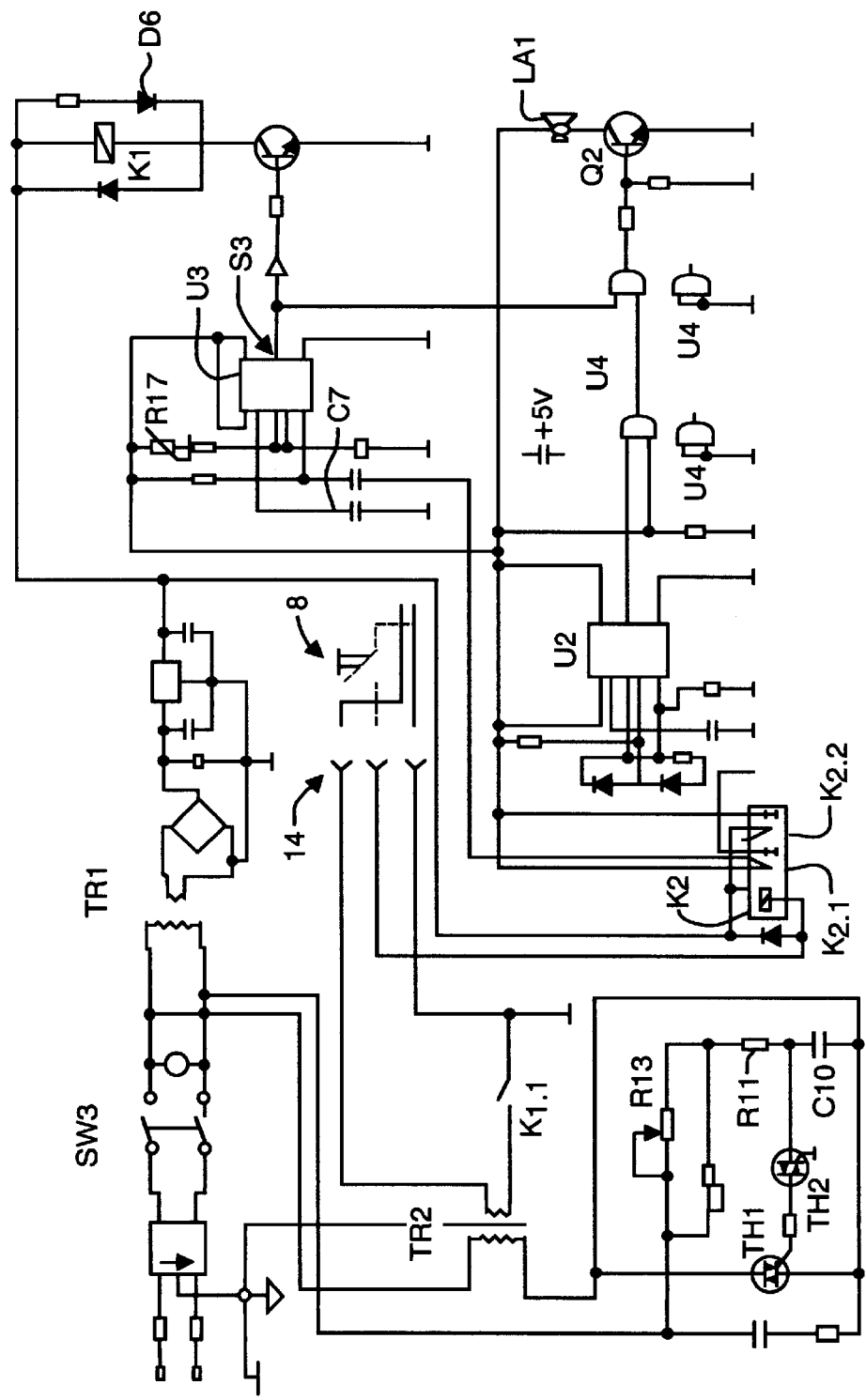
FIG. 3 is a circuit diagram of the electronic circuit.

FIGS. 2 and 3 show the electronic power and control circuit, which is generally comprised of a current (power) supply A, an adjustment circuit B, a control circuit C and an automatic cut-out circuit D. The electronic circuit can further include an optical and sound signalling circuit E, which will be discussed below.

The current (power) supply A comprises two transformers TR1 and TR2. The primaries of the transformers TR1 and TR2 are connected to the power source. The transformer TR1 is of a type having plates resistant to short-circuits. The secondary of the transformer TR1 delivers a voltage of 12V to the control circuit C, the cut-out circuit D and the signalling circuit E. The transformer TR2 is a toric transformer with a screen effect. The secondary of the transformer TR2 delivers a current of 20 A under 4V and is used to feed the heating electrodes (7).

The transformers TR1 and TR2 are charged by operating a main power switch (the switch SW3 of FIG. 3) which corresponds to the main switch (9) of FIG. 1. In addition to their power supplying function, the transformers TR1 and TR2 also fulfil a safety function; that being the isolation of patients and the main power supply.

The adjustment circuit B is coupled with the power supply A (phase feed) and is connected to the primary of the transformer TR2. The adjustment circuit B is generally comprised of a triac TH1, a diac TH2 and a quadrature circuit R11, C10. The triac TH1 switches from 0 to a maximum value on each cycle of the current in an extremely short period of time. This period (the "locking time") is adjusted by the diac TH2 and the potentiometer R13, which is operated responsive to the adjustment knob (12). The knob (12) is calibrated from 1 to 10, with each graduation corresponding to a predetermined amount of current for a given size of clamp.

By way of example, for a charge between electrodes of 0.1 W and 50 W and a nominal current of 1 A, the voltage measurements on positions 1, 5 and 10 of the knob (12) are 0.9V±20%, 1.4V±20% and 2.0V±20%, respectively.

The positions 1 to 5 are used for a range of monocortical and bicortical clamps of different sizes, having an alloy content of between 0.8 g and 1.7 g. The positions 6 to 10 are used for a range of epiphysial clamps having an alloy content of up to 2.8 g.

The control circuit C operates to co-ordinate the various functions of the device. Heating of the clamp is triggered by the control switch (8), which drives the relay K2. The contact $k_{2.1}$ of the relay K2 puts the capacitor C7 at zero volts. At the same time, the contact $k_{2.2}$ of the relay K2 puts the clock U3 at +12V.

Primarily for purposes of safety, the automatic cut-out circuit D operates to automatically cut off excessive heating (i.e., heating which has exceeded a predetermined period), thus limiting the amount of heat delivered to the clamp. In this way, any risk of necrosis is avoided, even if, for example, the surgeon forgets to turn off the switch (8).

The clock U3 is the main element of the circuit D. Operating times are adjusted (e.g., from 0 to 17s) by the counter (U3) and the variable resistor R17. A positive voltage is applied to the clock input so that when completed, the output (S3) of the clock has a potential and the relay K1 is released. The contact $k_{2.1}$ of the relay K1 then provides the desired timing sequence. The relay K1 is attracted and is released when the specific time has elapsed.

The optical and sound signalling circuit E includes the indicator light (11), the indicator light (13) and an acoustic signalling device LA1. The indicator (11) is illuminated to signal charging upon closure of the contacts SW3. The indicator (13), which is implemented with a LED (electroluminescent diode) D6, and the acoustic signalling device LA1 indicate the operating state for the device. To this end, the indicator (13) is illuminated when the control switch (8) is closed. At the same time, a voltage is established on the relay contact $k_{2.2}$ of the modulator U2. The modulator U2 is then activated, inducing modulation pulses in the sound signalling device LA1. The modulation pulses are sent, via gates U4, to the base of a transistor Q2 at intervals raised to 0 volts. If the control switch (8) is kept pressed when the prescribed time has elapsed, the indicator light (13) remains lit and the sound signalling device LA1 emits a continuous sound.

The electronic circuit is comprised of components which can be readily assembled by the skilled artisan.

Figure 4:
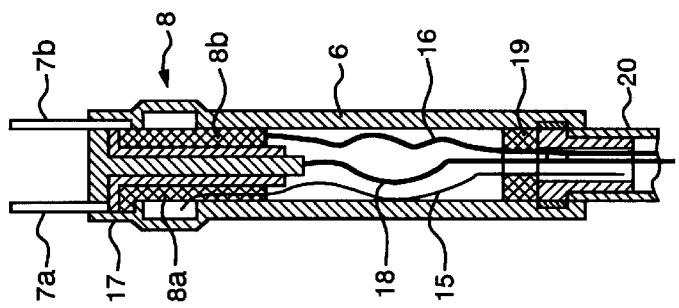
FIG. 4 is a cross-sectional view of the sleeve for the device of the present invention.

FIG. 4 shows a sectional view of the electrode carrier sleeve. As an example, the sleeve (6) shown in FIG. 4 has a hollow cylindrical shape. However, any other ergonomic shape which will facilitate handling of the device by the surgeon can be used.

Two conductor wires (15, 16) are connected to two contact zones (8a, 8b) of a light touch switch (8). The switch (8) is in turn connected to two heating electrodes (7a, 7b). The electrodes (7a, 7b) are kept parallel at the extremity of the sleeve (6), and are conventionally insulated by a non-conducting bush (17). A central conductor (18) is provided to ensure proper grounding.

The unit including the linking cord (4), the sleeve (6) and the plug (5) is made of materials which can be sterilized in an autoclave, withstanding temperatures of up to 134° C. The unit further includes a gasket (19) adjacent to the linking cord (4) to further allow for sterilization of the unit by immersion, if desired. A reinforcement piece (20) is provided at the outlet for the linking cord (4) to avoid kinking and to protect the conductor wires (15, 16, 18).

In use, the placement of a clamp by the surgeon proceeds as follows. The bone fragments to be joined are appropriately prepared and positioned. Drilling guides are then placed on both sides of the fracture and holes for receiving the clamps are drilled. The clamps are then placed, one after the other, in the drilled holes. The heating device is then charged, by turning on the main switch (9), and the position for the adjustment knob (12) is selected (according to the clamp which is being used). The sleeve of the device is then pressed on the clamp which is to be closed, and heating is initiated by depressing the switch (8) once the proper current has been established. An intermittent sound (signal) is then made by the device.

The applied current can be interrupted by the surgeon on closing of the clamp, or in default (e.g., at the end of five seconds), by the automatic cut-out circuit D. A continuous sound (signal) is then made by the device to warn the surgeon.

The heating device of the present invention provides the following improvements. Any type of clamp can be used. To this end, the spacing of the electrodes (e.g., 15 mm) allows dorsal parts of the smaller and average-sized clamps to be heated in a single application. For the larger clamps, one extremity of the clamp's dorsal portion is first heated, followed by heating of the other dorsal portion, which has the effect of successively folding the branches of the clamp. The amount of heat delivered to the clamp is limited. In particular, the amount of heat delivered to the clamp is limited so that the temperature reached by the alloy of the clamp is limited to 55° C. The period for applying heat to the clamp is also limited. The sleeve is totally impervious to liquids, and there is no risk of explosion because the electrical contacts used do not create any electric arcs.

The device of the present invention is most favorably used with heat-retractable shape memory clamps used in surgery, which are specially designed to be closed by the above-described heating device,. Such clamps will advantageously comprise a quantity of a nickel-titanium alloy which varies between 0.8 g and 2.8 g.

What is claimed is:

1. A device for heating and closing heat-retractable shape memory clamps used in surgery applications, wherein the device includes a unit containing an electronic power and control circuit supplied with line current which is coupled with a heating unit, wherein the electronic power and control circuit comprises a current supplying circuit, a system controller, an adjustment circuit, and an automatic cut-out circuit coupled to said adjustment circuit, and wherein the electronic power and control circuit operates to deliver one of a plurality of different and predetermined quantities of heat corresponding to a different and predetermined configuration for the clamps.

2. The device of claim 1 wherein the electronic power and control circuit limits the amount of heat delivered to the clamps so that the temperature generated in the clamps does not exceed a maximum value.

3. The device of claim 2 wherein the maximum value for the temperature is 55° C.

4. The device of claim 1 wherein the cut-out circuit automatically cuts the heat applied to the clamps at the end of a predetermined maximum time.

5. The device of claim 4 wherein the maximum time is limited to 5 seconds.

6. The device of claim 1 wherein the electronic power and control circuit automatically limits the voltage supplied to the heating unit and the amount of time that the voltage is supplied to the heating unit.

7. The device of claim 1 wherein the electronic power and control circuit further includes a sound signaling circuit, and wherein the sound signaling circuit emits a first sound signal during heating of the clamps and a second sound signal different from the first sound signal for heating of the clamps which exceeds a maximum heating time.

8. The device of claim 1 wherein the heating unit includes a linking cord, one end of which has a plug which is removably receivable in an outlet associated with the unit containing the electronic power and control circuit and another end of which has a sleeve which includes two heating electrodes and a control switch electrically coupled with the heating electrodes, and wherein the plug, the linking cord and the sleeve are sterilizable in an autoclave to form a sterilized unit.

9. The device of claim 8 wherein the control switch has touch-sensitive contacts.

10. The device of claim 8 wherein the sterilized unit is a sealed unit.

11. The device of claim 10 wherein the sleeve includes a gasket for coupling the linking cord with the sleeve.

12. The device of claim 8 wherein the heating electrodes are separated by a spacing of approximately 15 mm.

13. A device for heating and closing heat-retractable shape memory clamps used in surgery applications, wherein the device includes an electronic power and control circuit supplied with line current which is coupled with a heating unit, wherein the electronic power and control circuit comprises a current supplying circuit, a system controller, an adjustment circuit, and an automatic cut-out circuit coupled to said adjustment circuit, and wherein the electronic power and control circuit operates to deliver one of a plurality of different and predetermined quantities of heat corresponding to a different and predetermined configuration for the clamps.

14. The device of claim 13 wherein the electronic power and control circuit limits the amount of heat delivered to the clamps so that the temperature generated in the clamps does not exceed a maximum value.

15. The device of claim 14 wherein the maximum value for the temperature is 55° C.

16. The device of claim 13 wherein the cut-out circuit automatically cuts the heat applied to the clamps at the end of a predetermined maximum time.

17. The device of claim 16 wherein the maximum time is limited to 5 seconds.

18. The device of claim 13 wherein the electronic power and control circuit automatically limits the voltage supplied to the heating unit and the amount of time that the voltage is supplied to the heating unit.

19. The device of claim 13 wherein the heating unit includes a linking cord, one end of which has a plug which is removably receivable in an outlet associated with the electronic power and control circuit and another end of which has a sleeve which includes two heating electrodes and a control switch electrically coupled with the heating electrodes, wherein the plug, the linking cord and the sleeve are sterilizable in an autoclave to form a sterilized unit.

20. The device of claim 19 wherein the control switch has touch-sensitive contacts.

21. The device of claim 19 wherein the sterilized unit is a sealed unit.

22. The device of claim 21 wherein the sleeve includes a gasket for coupling the linking cord with the sleeve.

23. The device of claim 19 wherein the heating electrodes are separated by a spacing of approximately 15 mm.

* * * * *